United States Patent [19]
Green et al.

[11] 3,933,812
[45] Jan. 20, 1976

[54] CERTAIN 1,4-BIS-(MORPHOLINO)-2-BUTENE-CONTAINING CONDENSATION PRODUCTS AND THEIR PREPARATION

[75] Inventors: Harold A. Green, Havertown, Pa.;
John J. Merianos, Jersey City;
Alfonso N. Petrocci, Glen Rock,
both of N.J.

[73] Assignee: Millmaster Onyx Corporation, New York, N.Y.

[22] Filed: July 7, 1975

[21] Appl. No.: 593,736

Related U.S. Application Data

[60] Division of Ser. No. 511,759, Oct. 3, 1974, which is a continuation-in-part of Ser. No. 425,931, Dec. 18, 1973, Pat. No. 3,874,870.

[52] U.S. Cl. ............ 260/246 B; 71/67; 260/87.5 R; 260/239 B; 260/268 PL; 260/583 G; 424/244
[51] Int. Cl.$^2$ ........................................ C07D 295/12
[58] Field of Search ................................ 260/246 B

*Primary Examiner*—R. Gallagher
*Assistant Examiner*—Jose Tovar
*Attorney, Agent, or Firm*—Arthur A. Jacobs, Esq.

[57] ABSTRACT

Anti-Microbial Quaternary Ammonium Co-Polymers formed by the condensation of at least two di-functional tertiary amines and a molar quantity of 1,4-dihalo-2-butene that is equal to the molar sum of the di-functional tertiary amines in the mixture.

4 Claims, No Drawings

CERTAIN 1,4-BIS-(MORPHOLINO)-2-BUTENE-CONTAINING CONDENSATION PRODUCTS AND THEIR PREPARATION

This is a division of co-pending application Ser. No. 511,759, filed Oct. 3, 1974, which is a continuation-in-part of application Ser. No. 425,931, filed Dec. 18, 1973 and now issued as U.S. Pat. No. 3,874,870, dated Apr. 1, 1975.

This invention relates to a new class of microbiocidal agents. More particularly, the products of this invention are co-polymerization products made by condensing a mixture of two or more difunctional tertiary amines and a molar quantity of 1,4-dichloro-2-butene that is equal to the molar sum of the difunctional tertiary amines in the mixture.

The difunctional tertiary amines used in making the products of this invention are of the type

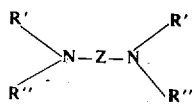

where Z consists of from one to three divalent aliphatic radicals of two to 10 carbon atoms which may contain zero to two double bonds or zero to two hydroxy substituents; wherein R' and R'' are either the same or different and wherein they may be (a) primary or secondary alkyls having one to 20 carbon atoms, where the sum of the carbon atoms in R' and R'' is no greater than 36, (b) hydroxy or dihydroxy derivatives of the aforesaid primary or secondary alkyls, (c) benzyl, (d) alkyl benzyl or (e) combined with N to form a heterocyclic group of either five, six or seven atoms.

One of the features of the co-polymers of the present invention is that the quaternary ammonium moieties are part of the long polymeric chain rather than being quaternary ammonium moieties on branches that are bonded to the polymeric chain.

Another feature of the present invention is that the copolymer is a unique reaction product and not a mere mechanical mixture of separate polymers. Therefore, the co-polymers of this invention cannot be separated into constituent components, as would be the case if they were mere mechanical mixtures.

Another feature of the present invention is that the primary chemical units comprising the polymeric chain are not identically repetitive as they would be if the product were an ordinary polymer. On the contrary, the several primary chemical units of the co-polymer are randomly distributed in the polymeric chain.

All of the above-described characteristics of the present invention are attained by causing a homogeneous mixture or solution of two or more difunctional tertiary amines to react with a molar quantity of 1,4-dichloro-2-butene which is equal to the molar sum of all of the components in the homogeneous mixture or solution of difunctional tertiary amines.

In this manner, if a homogeneous mixture or solution of 1,4-bis-(dimethylamino)-2-butene having the structure $(CH_3)_2 - N-CH_2 - CH = CH - CH_2 - N - (CH_3)_2$ and N,N'-dimethyl piperazine having the structure

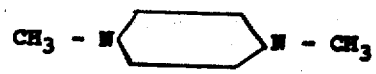

is reacted with a molar quantity of 1,4-dichloro-2-butene having the structure $Cl - CH_2 - CH = CH - CH_2 - Cl$ equal to the molar sum of the two difunctional tertiary amines, the two primary units which are part of the polymeric chain would be: $-CH_2 CH = CH - CH_2 - N^+(CH_3)_2 - CH_2 - CH = CH - CH_2 N^+(CH_3)_2 -$ and

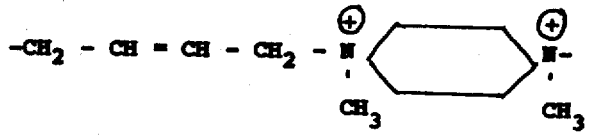

The ratio of the number of each of these units in the polymeric chain is very close to the molar ratio of the two difunctional tertiary amines in the starting mixture or solution, but the sequential order in which these two units appear in the polymeric chain is completely random, and therefore not identically repetitive.

The co-polymeric products of this invention are very effective microbiocides for use in controlling the microbial growth in circulatory and standing waters. They can, therefore, be used for the antimicrobial treatment of industrial waters, cooling tower water, humidifier water, swimming pools, and the like, as well as for general usage.

The following examples are illustrative of the present invention.

EXAMPLE 1

7.1 grams of 1,4-bis-(dimethylamino)-2-butene (0.05 mole) and 5.6 grams of diazabicyclo (2.2.2) octane (0.05 mole) were dissolved in 25 grams of water, and to the solution were added dropwise 12.5 grams of 1,4-dichloro-2-butene (0.1 mole) at such a rate as to keep the temperature at about 60°C-70°C. After addition was complete, and the exothermic reaction has subsided, the mixture was heated in a steam bath for about 1 hour, at which time analysis for ionic chloride showed that the reaction was about 98% to 100% complete. The resulting solution contained about 50% by weight of active co-polymer.

The same procedure was repeated, using as the mixtures of difunctional tertiary amines (a) 0.05 mole 1,4-bis-(morpholino)-2-butene and 0.05 mole of N,N' dimethylpiperazine, (b) 0.05 mole of diazabicyclo (2.2.2) octane and 0.05 mole of 1,4-di-(N-homopiperidino)-2-butene, (c) 0.05 mole of 1,4-bis-(dimethylamino)-2-butene and 0.05 mole of N,N,N',N'-tetramethyl ethylenediamine. In each synthesis, the weight of water used as a solvent was approximately equal to the sum of the weights of the two difunctional tertiary amines and 1,4-dichloro-2-butene, so that the final mixture contained about 50% by weight of active co-polymer.

EXAMPLE 2

12.8 grams of 1,4-bis-(dimethylamino)-2-butene (0.09 moles) and 1.14 grams of N,N'-dimethyl piperazine (0.01 mole) were dissolved in 26 grams of water, and to the solution were added dropwise 12.5 grams of 1,4-dichloro-2-butene at such a rate as to keep the temperature at about 60°C–70°C. After addition was completed, and the exothermic reaction had subsided, the mixture was heated on a steam bath for about 1 hour, at which time analysis for ionic chloride showed that the reaction was about 98% to 100% complete. The resulting solution contained about 50% by weight of active co-polymer.

The same procedure was repeated using as the mixtures of difunctional tertiary amines (a) 0.08 mole of 1,4-bis-(dimethylamino)-2-butene and 0.02 mole of 1,4-bis-(N-morpholino)-2-butene, (b) 0.08 mole of 1,4-bis-(dimethylamino)-2-butene and 0.02 mole of 1,4-bis-(N-homopiperidino)-2-butene, (c) 0.07 mole of 1,4-bis-(dimethylamino)-2-butene and 0.03 mole of 1,4-bis-(methyl dodecyl amino)-2-butene, and (d) 0.09 mole of 1,4-bis-(dimethylamino)-2-butene and 0.01 mole of 1,4-bis-(methyl dodecylamino)-2-butene.

In each synthesis, the weight of the water used as a solvent was approximately equal to the sum of the weights of the two difunctional tertiary amines and 1,4-dichloro-2-butene, so that the final mixture contained about 50% by weight of active co-polymer.

EXAMPLE 3

11.40 grams of 1,4-bis-(dimethylamino)-2-butene (0.08 mole), 1.2 grams of N,N'-dimethyl piperazine (0.01 mole) and 2.3 grams of 1,4-bis-(N-morpholino)-2-butene (0.01 mole) were dissolved in 27 grams of water, and to the solution were added dropwise 12.5 grams of 1,4-dichloro-2-butene at such a rate as to keep the temperature at about 60°–70°C. After addition was complete, and the exothermic reaction had subsided, the mixture was heated on a steam bath for about 1 hour, at which time analysis for ionic chloride showed that the reaction was about 98%–100% complete. The resulting solution contained about 50% by weight of active co-polymer.

The same procedure was repeated using as the mixtures of difunctional tertiary amines (a) 0.08 mole of 1,4-bis-(dimethylamino)-2-butene, 0.01 mole of 1,4-bis-(N-homopiperidino)-2-butene and 0.01 mole of N,N'-dimethyl piperazine, and (b) 0.08 mole of 1,4-bis-(dimethylamino)-2-butene, 0.01 mole of N,N'-dimethylpiperazine and 0.01 mole of 1,4-diazabicyclo (2.2.2) octane.

In each synthesis, the weight of water used as a solvent was approximately equal to the sum of the weights of the three difunctional tertiary amines and 1,4-dichloro-2-butene, so that the final mixture contained about 50% by weight of active copolymer.

EXAMPLE 4

11.1 grams of 1,4-di-(N-homopiperazino)-2-butene (0.05 mole) and 5.6 grams of 1,4-diazabicyclo (2.2.2) octane (0.05 mole) were dissolved in about 20 grams of isopropanol, and to the solution was added 12.5 grams of 1,4-dichloro-2-butene over a period of about 15 minutes, or at a rate which keeps the solvent refluxing gently. After the exothermic reaction subsided, the mixture was maintained under reflux for about 1 hour. It was then cooled to room temperature, and the precipitate was separated from the mother liquors by filtration. The solid copolymer, which was produced after drying, was substantially free from impurities caused by side reactions or by adsorbtion of unreacted starting materials, thereby making it easier to purify for use in cosmetics, cosmetic emulsions or other vehicles intended for use on the human body.

The same product, in about the same yield was obtained when acetone replaced isopropanol as the solvent.

EXAMPLE 5

Various representative co-polymers were made in accordance with the specifications and examples of this invention for antimicrobial testing. The co-polymeric products are related to their numbers as follows, it being understood that the ratio of difunctional tertiary amines is given in moles, and the molar quantity of 1,4-dichloro-2-butene is equal to the molar sum of the amines.

| Product 1 | 90% | 1,4-bis (dimethylamino)-2-butene |
| | 10% | 1,4-diazabicyclo (2.2.2) octane |
| Product 2 | 90% | 1,4-bis (dimethylamino)-2-butene |
| | 10% | N,N'-dimethylpiperazine |
| Product 3 | 80% | 1,4-bis-(dimethylamino)-2-butene |
| | 20% | 1,4-di-(N-morpholino)-2-butene |
| Product 4 | 80% | 1,4-bis-(dimethylamino)-2-butene |
| | 10% | 1,4-bis-(N-morpholino)-2-butene |
| | 10% | N,N'-dimethylpiperazine |
| Product 5 | 80% | 1,4-bis-(dimethylamino)-2-butene |
| | 10% | 1,4-bis-(N-homopiperidino)-2-butene |
| | 10% | N,N'-dimethylpiperazine |
| Product 6 | 80% | 1,4-bis-(dimethylamino)-2-butene |
| | 10% | 1,4-diazabicyclo (2.2.2) octane |
| | 10% | N,N'-dimethylpiperazine |
| Product 7 | 50% | 1,4-bis-(1,4-dimethylamino)-2-butene |
| | 50% | N,N,N',N'-tetramethylethylenediamino |
| Product 8 | 80% | 1,4-bis-(dimethylamino)-2-butene |
| | 20% | 1,4-bis-(N-homopiperidino)-2-butene |
| Product 9 | 70% | 1,4-bis-(dimethylamino)-2-butene |
| | 30% | 1,4-bis-(methyldodecylamino)-2-butene |
| Product 10 | 90% | 1,4-(dimethylamino)-2-butene |
| | 10% | 1,4-bis-(methyldodecylamino)-2-butene |

The broth dilution method was used to determine the minimum inhibitory level of the several representative mixtures of polymeric quaternary products against a variety of bacteria. The organisms chosen were *Escherechia coli, Pseudomonas aeruginosa, Staphyllococcus aureus,* and *Streptococcus faecalis.*

A nutrient broth for testing *E. coli, P. aeruginosa* and *S. aureus* was made up by dissolving 5.0 grams of Beef extract
5.0 grams of sodium chloride
10.0 grams of Peptone per liter of solution.

The nutrient broth for testing *S. faecalis* was made up by dissolving 2.5 grams of dextrose
5.0 grams of sodium chloride
2.5 grams of di-potassium phosphate
20.0 grams of peptone per liter of water.

Each broth used for testing was sterilized for 15 minutes at 15 pounds of steam.

To 9.0 ml. of broth, 1.0 ml. of aqueous solution of each compound to be tested was added in appropriate concentrations to make final mixtures contain 500, 250, 100, 50, 25 ppm respectively. Then 0.01 ml. of a 24 hour bacterial broth culture was added into each tube to give a final bacterial count of $(1-10) \times 10^{-8}$ organisms per ml. of the test bacteria.

The tubes so inoculated were incubated at 37°C, and the results were recorded for turbidity growth after 48 and 96 hours.

The lowest concentration of experimental product being tested which prevented microscopic growth of test bacteria, was considered to be the minimum inhibitory level for that specific bacteria being tested.

The results of the tests, portraying the relationship between minimum inhibitory concentrations and test organisms, are shown in the following table:

Table 1

| Product | Minimum Inhibitory Level (in ppm) | | | |
|---|---|---|---|---|
| | E. coli | P. aeruginosa | S. aureus | S. faecalis |
| Product 1 | 100 | 100 | 100 | 100 |
| Product 2 | 100 | 100 | 50 | 50 |
| Product 3 | 100 | 100 | 50 | 50 |
| Product 4 | 100 | 100 | 100 | 100 |
| Product 5 | 50 | 50 | 50 | 50 |
| Product 6 | 100 | 500 | 50 | 50 |
| Product 7 | 100 | 500 | 100 | 100 |
| Product 8 | 100 | 100 | 50 | 50 |
| Product 9 | 50 | 50 | 50 | 50 |
| Product 10 | 50 | 50 | 50 | 50 |

The tests give clear indication that the co-polymeric quaternary products of this invention are effective inhibitors of bacterial growth, at low concentrations.

EXAMPLE 6

In order to test the foaming properties of the co-polymers of this invention, the extremely vigorous "Waring Blender Test" was used. The procedure of this test was as follows:

A graduated cylinder is rinsed with distilled water and 100 ml of aqueous solution is added down the walls of the cylinder so as to cause no foam. The blender is turned on at high speed for exactly 5 seconds, and upon turning the blades off, timing is started with a stop watch and at the same time the foam height from the 100 ml is read and noted.

The foam half-life is defined and noted as the time it takes for the liquid to drain out of the foam and reach the 50 ml mark.

The test results were as follows:

Table 2

| Compound | Waring Blender Foam Test at 25°C. Concentration 100 ppm. | |
|---|---|---|
| | Distilled Water Foam Height/Half-Life (mm) / (sec.) | 300 ppm Hard Water Foam Height/Half-Life (mm) / (sec.) |
| Product 1 | 0/0 | 0/0 |
| Product 2 | 0/0 | 0/0 |
| Product 3 | 0/0 | 0/0 |
| Product 4 | 0/0 | 0/0 |

The test results show that the quaternary ammonium copolymers are non-foaming in distilled water, and in hard water.

The invention claimed is:

1. A product formed by the condensation of a mixture of difunctional tertiary amines and a molar quantity of 1,4-dichloro-2-butene that is substantially equal to the molar sum of the mixture of the difunctional tertiary amines, said mixture of difunctional tertiary amines being selected from the group consisting of (a) 1,4-bis-(morpholino)-2-butene and N,N'-di-lower alkyl piperazine, (b) 1,4-bis-(dimethylamino)-2-butene and 1,4-bis-(N-morpholino)-2-butene, and (c) 1,4-bis-(dimethylamino)-2-butene, N,N'-di-lower alkyl piperazine and 1,4-bis-(N-morpholino)-2-butene.

2. The product of claim 1 wherein N,N'-di-lower alkyl piperazine is N,N'-dimethyl piperazine.

3. A method of making a product which comprises the step of condensing a mixture of difunctional tertiary amines and a molar quantity of 1,4-dichloro-2-butene that is substantially equal to the molar sum of the mixture of the difunctional tertiary amines, said mixture of difunctional tertiary amines being selected from the group consisting of (a) 1,4-bis-(morpholino)-2-butene and N,N'-di-lower alkyl piperazine, (b) 1,4-bis-(dimethylamino)-2-butene and 1,4-bis-(N-morpholino)-2-butene, and (c) 1,4-bis-(dimethylamino)-2-butene, N,N'-di-lower alkyl piperazine and 1,4-bis-(N-morpholino)-2-butene.

4. The method of claim 3 wherein N,N'-di-lower alkyl piperazine is N,N'-dimethyl piperazine.

* * * * *